United States Patent [19]

Hayashi et al.

[11] 4,439,413

[45] Mar. 27, 1984

[54] RADIOACTIVE DIAGNOSTIC AGENT FOR BONE SCANNING AND NON-RADIOACTIVE CARRIER THEREFOR

[75] Inventors: Miki Hayashi; Keietsu Takahashi, both of Takarazuka; Masaaki Hazue, Amagasaki, all of Japan

[73] Assignee: Nihon Medi-Physics Company, Ltd., Japan

[21] Appl. No.: 300,876

[22] Filed: Sep. 11, 1981

[30] Foreign Application Priority Data

Sep. 13, 1980 [JP] Japan .............................. 55/127690

[51] Int. Cl.$^3$ ...................... A61K 43/00; A61K 49/00
[52] U.S. Cl. ............................................. 424/1.1; 424/9
[58] Field of Search ........................................ 424/1, 9

[56] References Cited

U.S. PATENT DOCUMENTS

| | | | |
|---|---|---|---|
| 4,229,427 | 10/1980 | Whitehouse | 424/1 |
| 4,232,000 | 11/1980 | Fawzi | 424/1 |
| 4,233,284 | 11/1980 | Fawzi | 424/1 |
| 4,234,562 | 11/1980 | Tofe et al. | 424/1 |
| 4,247,534 | 1/1981 | Bevan | 424/1 |

OTHER PUBLICATIONS

Barnes et al., Int. J. Appl. Rad. Isotopes, 32(3), 174–175 (1981).
Domstad et al., Radiology, 136(1), 209–211 (1980).

*Primary Examiner*—Christine M. Nucker
*Attorney, Agent, or Firm*—Jones, Tullar & Copper

[57] ABSTRACT

A radioactive diagnostic agent for bone scanning, which comprises $^{99m}$Tc and a non-radioactive carrier comprising (A) at least one chosen from methanehydroxydiphosphonic acid and their salts and (B) at least one reducing agent for pertechnetates in a weight ratio of about 1:1 to 7:1 and prevents the accumulation of radioactivity in liver so that definite diagnosis can be assured.

16 Claims, No Drawings

RADIOACTIVE DIAGNOSTIC AGENT FOR BONE SCANNING AND NON-RADIOACTIVE CARRIER THEREFOR

The present invention relates to a radioactive diagnostic agent for bone scanning and a non-radioactive carrier therefor. More particularly, it relates to a $^{99m}$Tc-labeled radioactive diagnostic agent for bone scanning, which prevents the accumulation of radioactivity in liver and makes definite diagnosing possible, and a non-radioactive carrier therefor.

The diagnostic detection of bone diseases accompanied with abnormality of calcium hydroxyapatite such as metastasis of cancer to bone, especially at the initial stage, is highly desired. For this purpose, however, the conventional diagnostic system using X-ray perspective inspection technique is unsatisfactory.

Attempts to use radioactive diagnostic agents for said purpose were made with compositions comprising radioactive isotopes such as fluorine-18 and strontium-85. These isotopes have a tendency to be selectively accumulated at the physiologically active sites such as a joint site or a tumor site and are recognized to be useful for detecting skeletal metastasis of cancer. However, fluorine-18 is limited in the use because of its too short half life (i.e. 110 minutes). Further, its radioactive gamma ray energy is so high (i.e. 511 KeV) as being unsuited for imaging with a usual scintillation camera. On the other hand, strontium-85 has a too long half life (i.e. 65 days) and, when administered within an allowable exposure limit, requires a very long time to obtain a scintigram permitting diagnosis. As above, fluorine-18 and strontium-85 are not suitable for radionuclear diagnosis, and the focus of study in this field of the nuclear medicine has been directed to technetium-99m ($^{99m}$Tc).

$^{99m}$Tc has an adequate half life of six hours. Further, the energy of the gamma ray emitted by $^{99m}$Tc (140 KeV) is most suitable to get a scintigram. Moreover, it has a merit of being usable at any optional time due to the popularization of a technetium-99m generator. Commercialized $^{99m}$Tc as well as $^{99m}$Tc eluted from a technetium-99m generator are considered to be in a heptavalent state and as such can not combine with a carrier for bone scanning. But, by reducing to a lower valency state with a suitable reducing agent, $^{99m}$Tc comes to be readily combined with such carrier. $^{99m}$Tc per se has no property to be selectively accumulated in bone but, when combined with a suitable bone-seeking carrier, can be accumulated on a skeleton site so as to make bone imaging possible.

In this respect, U.S. patent 4,016,249 discloses the use of $^{99m}$Tc in combination with a certain water-soluble phosphate and a reducing agent for accumulation of the radio-activity of $^{99m}$Tc on a skeleton site. Also, U.S. Pat. No. 3,983,227 discloses the use of a radioactive pertechnetate solution incorporated with a reductive salt and an organic phosphonate for bone scanning. Further, Japanese Patent Publication (unexamined) No. 1040/1977 discloses that various organic phosphonates are usable in radioactive diagnostic agents for bone scanning.

According to Japanese Patent Publication (unexamined) No. 54439/1980, the use of a methanehydroxydiphosphonate in a radioactive diagnostic agent for bone scanning comprising a pertechnetate and a reducing agent therefor can provide a sharp bone mineral image and an excellent lesion detection, when the weight ratio of the methanehydroxydiphosphonate and the reducing agent is in a range of about 10:1 to 15:1, particularly of about 8:1 to 13:1.

Up to the present time, various radioactive diagnostic agents comprising $^{99m}$Tc and organic phosphonates or inorganic phosphates have appeared in the market and are subjected to the practical use. The greatest problem common to these radioactive diagnostic agents is the retention of the radioactive component in various organs. Particularly when the accumulation of radioactivity in liver exceeds a certain level, the large portion of the skeleton scintigram is made obscure. Because of this reason, a great effort has been made to provide a radioactive diagnostic agent which suppresses the uptake of the radioactivity in liver.

As a result of the extensive study, it has now been found that a radioactive diagnostic agent comprising a pertechnetate, a reducing agent therefor and a methanehydroxydiphosphonate wherein the weight ratio of the methanehydroxydiphosphonate and the reducing agent is kept in a certain specific range is quite effective in detection of any lesion in the skeleton site and can provide a sharp and clear bone scintigram within a short time after the administration without any serious uptake of radioactivity in liver.

When, for instance, aqueous solutions comprising $^{99m}$Tc in the form of pertechnetate with methanehydroxydiphosphonic acid and stannous chloride as the reducing agent for the pertechnetate in various weight proportions were administered to rats by injecting into the tail vein, the proportion of the radioactivity concentrations in femur and in liver was varied with the said weight proportion as shown in the following table:

| Experiment No.*1 | Weight ratio of methanehydroxydiphosphonic acid and anhydrous stannous chloride | Ratio of radioactivity concentrations (%/g) in femur and in liver |
| --- | --- | --- |
| 1 | 0.7:1 | 18.9 |
| 2 | 1:1 | 56 |
| 3 | 1.5:1 | 38 |
| 4 | 1.9:1 | 15 |
| 5 | 5.0:1 | 2.1 |
| 6 | 7.0:1 | 1.5 |
| 7 | 10.0:1 | 0.8 |
| 8 | 12.4:1 | 0.6 |

Note:
*1 Using anhydrous stannous chloride (1 mM concentration) as the reducing agent and L-ascorbic acid (0.167 mM concentration) as the stabilizer, an injection solution containing $^{99m}$Tc in a concentration of 1.25 mCi/ml was prepared. The injection solution was administered to groups of SD strain female rats, each group consisting of three rats, in an amount of 0.25 mCi per rat. After 2 hours, the rats were sacrificed, and the desired organs were taken out and subjected to measurement of radioactivity. The values are the average in each group.

With respect to the radioactive diagnostic agent comprising a pertechnetate, an organic phosphonate and a reducing agent for the pertechnetate, the suppression of the uptake of radioactivity in liver has heretofore been attempted by limiting the amount of the reducing agent to the minimum. For instance, a typical example of radioactive diagnostic agents as commercially available contains the organic phosphonate and the reducing agent in a weight ratio of about 10:1 to 40:1. Further, for instance, Japanese Patent Publication (unexamined) No. 54439/1980 relating to a $^{99m}$Tc-labeled radioactive diagnostic agent using methanehydroxydiphosphonic acid teaches the weight ratio of the methanehydroxydiphosphonic acid and the reducing agent being from about 8:1 to 13:1 as the preferred range.

Contrary to the past attempt as above, the results in the said table show that the lower weight ratio of methanehydroxydiphosphonic acid and stannous chloride as the reducing agent produces remarkable suppression. More specifically, the larger proportion of methanehydroxydiphosphonic acid to stannous chloride increases the uptake of radioactivity into liver, whereby the ratio of the radioactivity concentrations in bone and in liver is lowered, and the clarity and detectability of the scintigram or scanning image are deteriorated.

According to the present invention, there is provided a non-radioactive carrier, which comprises (A) at least one chosen from methanehydroxydiphosphonic acid and their salts and (B) at least one reducing agent for pertechnetate in a weight ratio of about 1:1 to 7:1. There is also provided a radioactive diagnostic agent for bone scanning, which comprises $^{99m}$Tc in the form of pertechnetate and the said non-radioactive carrier.

Methanehydroxydiphosphonic acid is representable by the formula:

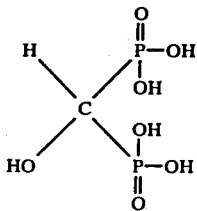

and its salt may be any pharmaceutically acceptable, water-soluble one. Specific examples are alkali metal salts (e.g. monosodium salt, disodium salt, trisodium salt, tetrasodium salt, dipotassium salt), ammonium salts (e.g. diammonium salt), etc. The most preferred is a mixture of methanehydroxydiphosphonic acid and its sodium salt(s).

As the reducing agent for pertechnetate, there is usually employed a stannous salt, i.e. a salt of divalent tin ion ($Sn^{++}$). Specific examples are stannous halides (e.g. stannous chloride, stannous fluoride), stannous sulfate, stannous nitrate, stannous acetate, stannous citrate, etc. $Sn^{++}$ ion-bearing resins such as ion-exchange resins charged with $Sn^{++}$ ion are also usable.

In addition to the components (A) and (B), the carrier of the invention may preferaly comprise (C) a reductive stabilizer for preventing the oxidation of a stannous salt and/or inhibiting the re-oxidation of $^{99m}$Tc as once reduced. The reductive stabilizer may also be effective in suppressing the production of any unfavorable impurity in the carrier or the diagnostic agent prepared by its use. The stabilizer may be any pharmaceutically acceptable one, particularly suitable for intravenous injection. Specific examples are ascorbic acid, erythorbic acid, gentisic acid, etc. These may be used in a free form or in the form of salt or ester. Further, any conventional additive(s) such as an isotonizing agent (e.g. sodium chloride) or a preservative (e.g. benzyl alcohol) may be incorporated in the carrier. In general, the components (B) and (C) are preferred to be water-soluble, but this is not essential.

On preparation of the non-radioactive carrier of the invention, the essential components (A) and (B) may be mixed in an optional order, if necessary, with any optional component(s) such as the component (C). The carrier may be formulated in the form of powdery preparation, particularly of lyophilized powder, or in the form of liquid preparation, particularly of aqueous solution. In the thus prepared carrier, the components (A) and (B) should be included in a weight ratio of about 1:1 to 7:1, preferably of about 1:1 to 3:1. In case of the component (B) being used in a larger proportion than the said upper limit, the ratio of the radioactivity concentrations in bone and in liver is still relatively high but that in bone and in blood is considerably lowered. Thus, the disappearance of radioactivity from blood becomes very late, and a sharp image on the scintigram is hardly obtainable. In case of the component (B) being used in a smaller proportion than the said lower limit, the ratio of the radioactivity concentrations in bone and in liver becomes less than 1, which is the lowest limit for obtaining a sharp skeletal image. When the component (C) is incorporated therein, its amount is usually from about 1 to 1/20 part by weight, preferably from about ½ to 1/5 part by weight, to 1 part by weight of the component (A), although any particular limitation is not present.

For preparation of the radioactive diagnostic agent of the invention, $^{99m}$Tc in the form of pertechnetate may be contacted with the non-radioactive carrier. $^{99m}$Tc in the form of pertechnetate is used normally in its aqueous solution, which may include additionally any conventional additive(s) such as an isotonizing agent (e.g. sodium chloride) or a preservative (e.g. benzyl alcohol). While the concentration of $^{99m}$Tc in the aqueous solution as the radioactive diagnostic agent is not particularly limited, it should have such a concentration as can afford a sufficient radioactivity concentration for bone scanning, preferably from about 0.1 to 50 mCi in about 0.5 to 5.0 ml at the time of administration. The amount of the carrier to be combined with $^{99m}$Tc in the form of pertechnetate may be such that the reducing agent in the carrier is sufficient to reduce said $^{99m}$Tc.

As the result of the combination of the non-radioactive carrier in a powdery form or in a liquid form with an aqueous solution comprising $^{99m}$Tc in the form of pertechnetate, there is prepared the $^{99m}$Tc-labeled radioactive diagnostic agent in situ. Naturally, the weight ratio of the components (A) and (B) in the diagnostic agent is from about 1:1 to 7:1. $Sn^{++}$ ions act on $^{99m}$Tc in a heptavalent state to reduce it to be in a tetravalent state.

As stated above, the $^{99m}$Tc-labeled radioactive diagnostic agent of the present invention suppresses the accumulation of radioactivity in liver so that a sharp and clear scintigram or scanning image is obtainable. Thus, definite diagnosis is made possible by the use of the radioactive diagnostic agent of the invention.

The following examples will illustrate the present invention in more detail. In these examples, methanehydroxydiphosphonic acid is referred to as "HMDP," and ethanehydroxydiphosphonic acid is referred to as "EHDP."

EXAMPLE 1

Preparation of the non-radioactive carrier using the disodium salt of HMDP and stannous chloride with L-ascorbic acid as the stabilizer:

Into sterilized water containing no pyrogen substance, nitrogen gas freed from bacteria through a filter of 0.2 μm in pore size was introduced to remove the dissolved oxygen. In 1 liter of this water, there were dissolved aseptically the disodium salt of HMDP (142 mg, 0.6 mmol), anhydrous stannous chloride (66 mg, 0.35 mmol) and L-ascorbic acid (35 mg, 0.2 mmol) under nitrogen stream, and the resulting solution was adjusted to a pH of 4 to 6 with sodium hydrogen carbonate. The resultant composition (referred to as "H.Sn.A.") was passed through a filter of 0.22 μm in pore size under nitrogen stream, and each 2.2 ml was filled in each ampoule, followed by sealing. The H.Sn.A. composition was colorless and transparent.

EXAMPLE 2

Preparation of the $^{99m}$Tc-labeled radioactive diagnostic agent using the H.Sn.A. composition:

The H.Sn.A. composition (1.5 ml) obtained in Example 1 was mixed with physiological saline water (1.5 ml) containing technetium-99m (15 mCi) in the form of sodium pertechnetate and stirred well. Thereafter, the mixture was allowed to stand for 15 minutes to give a diagnostic composition (referred to as "Tc-H.Sn.A.").

In order to check the labeling efficiency, the Tc-H.Sn.A. composition was developed on a cellulose acetate thin layer plate with a solvent mixture of a 2 M ammonium chloride solution and a 10 M urea solution in a volume ratio of 1:1 and scanned with a radiochromato-scanner. The radioactivity was detected as a single peak at Rf=0.97, and no other radioactive peak was observed. In the same thin layer chromatography system as above, technetium-99m in the form of pertechnetate was developed at Rf=0.7, and tin colloid labeled with technetium-99m remained at the original point. Thus, the labeling efficiency of the Tc-H.Sn.A. composition may be considered as 100%.

EXAMPLE 3

Distribution of the $^{99m}$Tc-labeled radioactive diagnostic agent in rat:

The Tc-H.Sn.A. composition (0.2 ml) obtained in Example 2 was intravenously administered to each of SD strain female rats, which were dissected 1 hour, 2 hours or 3 hours after the administration. The organs were taken out to measure the radioactivity in each organ and the weight of each organ. The radioactivity concentration in each organ as determined is shown in Table 1. The radioactivity concentration ratios of bone/blood, bone/muscle and bone/liver were calculated and are also shown in Table 1.

TABLE 1

Distribution of Tc—H.Sn.A. in rat
(% to administered radioactivity per gram)

| Organ | 1 hr. after administration | 2 hrs. after administration | 3 hrs. after administration |
|---|---|---|---|
| Bone (femur) | 3.71 | 4.30 | 3.88 |
| Liver | 0.07 | 0.05 | 0.04 |
| Kidney | 0.52 | 0.87 | 0.32 |
| Muscle | 0.038 | 0.019 | 0.013 |
| Blood (1 ml) | 0.101 | 0.022 | 0.012 |
| Bladder[*1] | 47.6 | 46.8 | 54.4 |
| Bone/Muscle | 97.6 | 226.3 | 298.5 |
| Bone/Blood | 36.7 | 195.5 | 323.3 |
| Bone/Liver | 53.0 | 86.0 | 97.0 |

Note:
[*1]% to administered radioactivity.

For comparison, the distribution of $^{99m}$Tc-EHDP injection as a commercially available bone scanning radioactive diagnostic agent in rat was examined in the same manner as above, and the results are shown in Table 2.

TABLE 2

Ratio of radioactivity concentration of $^{99m}$Tc—EHDP in bone/muscle, bone/blood and bone/liver in rat

| Organ | 1 hr. after administration | 2 hrs. after administration | 3 hrs. after administration |
|---|---|---|---|
| Bone/Muscle | 67.3 | 105.3 | 172.5 |
| Bone/Blood | 38.4 | 78.6 | 109.9 |
| Bone/Liver | 41.2 | 55.6 | 76.3 |

It is well known to those skilled in the art that, in order to obtain a clear skeleton image within a short time after administration of a radioactive diagnostic agent for bone scanning, the ratios of bone/muscle, bone/blood and bone/liver should give higher values. The results in Tables 1 and 2 show that the Tc-H.Sn.A. composition is more excellent as a bone scanning radioactive diagnostic agent than the commercially available Tc-EHDP injection.

EXAMPLE 4

Stability of the non-radioactive carrier (i.e. the H.Sn.A. composition):

The H.Sn.A. composition obtained in Example 1 was stored at 4° to 10° C. for 2 months. Using the resultant composition, there was prepared a $^{99m}$Tc-labeled radioactive diagnostic agent in the same manner as in Example 2. As to this diagnostic agent, the labeling rate and the distribution in rat were examined in the same manner as in Examples 2 and 3. The obtained results were substantially the same as those with the non-radioactive carrier immediately after its production. Thus, no material difference was recognized between the H.Sn.A compositions immediately after the production and after the storage over a period of 2 months.

EXAMPLE 5

Stability of the $^{99m}$Tc-labeled radioactive diagnostic agent (i.e. the Tc-H.Sn.A. composition):

The Tc-H.Sn.A. composition obtained in Example 2 was stored at room temperature for 24 hours. As to this diagnostic agent, the labeling rate and the distribution in rat were examined in the same manner as in Examples 2 and 3. The obtained results were substantially the same as those with the diagnostic agent immediately after its production. Thus, no material difference was recognized between the Tc-H.Sn.A. composition immediately after the production and after the storage over 24 hours. Since the half life of $^{99m}$Tc is 6 hours, the assurance of the stability for 24 hours is sufficient for the practical use.

EXAMPLE 6

Toxicity of the $^{99m}$Tc-labeled radioactive diagnostic agent (i.e. the Tc-H.Sn.A. composition):

The H.Sn.A. composition obtained in Example 1 was admixed with a physiological saline water containing $^{99m}$Tc radioactively attenuated in the form of sodium pertechnetate in a weight proportion of 1:1, and the resultant mixture was intravenously administered to groups of SD strain male and female rats, each group consisting of 10 animals, in an amount of 1 ml per 100 g of body weight (which corresponds to 300 times of the amount to be administered to human beings) and also to groups of ICR strain male and female mice, each group consisting of 10 animals, in an amount of 0.5 ml per 10 g of body weight (which corresponds to 1500 times of the amount to be administered to human beings). In the control groups having the same number of animals as above, the same volume of physiological saline water as above was administered intravenously. All the groups were bred for 10 days, and the variation of the body weight was recorded everyday. No significant difference was observed between the groups which received the Tc-H.Sn.A. composition and the control groups. After the observation over 10 days, all the animals were sacrificed, and any abnormality was not observed on any organ taken out from them. Thus, it is understood that the toxicity of the Tc-H.Sn.A. composition is extremely low.

What is claimed is:

1. A non-radioactive carrier, which comprises (A) methanehydroxydiphosphonic acid or a pharmaceutically acceptable water soluble salt thereof and (B) at least one reducing agent for pertechnetates in a weight ratio of about 1:1 to 7:1.

2. The carrier according to claim 1, wherein the weight ratio of the components (A) and (B) is from about 1:1 to 3:1.

3. The carrier according to claim 1, wherein the components (A) and (B) are both water-soluble.

4. The carrier according to claim 1, wherein the component (B) is a stannous salt.

5. The carrier according to claim 1, wherein the components (A) and (B) are dissolved in an aqueous medium.

6. The carrier according to claim 1, which is in a lyopholized powder state.

7. The carrier according to claim 1, which further comprises (C) a pharmaceutically acceptable reductive stabilizer.

8. The carrier according to claim 7, wherein the component (C) is the one chosen from ascorbic acid, erythorbic acid and gentisic acid, and their salts or esters.

9. The carrier according to claim 7, wherein the weight proportion of the components (A) and (C) is from about 1:1 to 20:1.

10. A radioactive diagnostic agent for bone scanning which comprises $^{99m}$Tc and a non-radioactive carrier which comprises (A) methanehydroxydiphosphonic acid or a pharmaceutically acceptable water soluble salt thereof and (B) at least one reducing agent for pertechnetates in a weight ratio of about 1:1 to 7:1.

11. A radioactive diagnostic agent for bone scanning which comprises $^{99m}$Tc in the form of pertechnetate and a non-radioactive carrier which comprises (A) methanehydroxydiphosphonic acid or a pharmaceutically acceptable water soluble salt thereof and (B) at least one reducing agent for pertechnetates in a weight ratio of about 1:1 to 7:1.

12. The diagnostic agent as in claim 10 or 11 wherein the weight ratio of components (A) and (B) is from about 1:1 to 3:1.

13. The diagnostic agent as in claim 10 or 11 wherein component (B) is a stannous salt.

14. The diagnostic agent as in claim 10 or 13 wherein the components (A) and (B) are dissolved in an aqueous medium.

15. The diagnostic agent as in claim 10 or 13 which is in a lyophilized powder form.

16. The diagnostic agent as in claim 10 or 11 which further comprises (C) a pharmaceutically acceptable reductive stabilizer.

* * * * *